United States Patent [19]
Adams et al.

[11] Patent Number: 5,316,016
[45] Date of Patent: May 31, 1994

[54] IMAGING BALLOON CATHETER AND METHODS FOR USE AND MANUFACTURE

[75] Inventors: Daniel O. Adams, Orono; Lixiao Wang, St. Paul; David J. Sogard, Edina; Gary L. Hendrickson, New Hope, all of Minn.

[73] Assignee: Scimed Life Systems, Inc., Maple Grove, Minn.

[21] Appl. No.: 909,772

[22] Filed: Jul. 7, 1992

[51] Int. Cl.⁵ .............................................. A61B 5/103
[52] U.S. Cl. .................................... 128/774; 602/96
[58] Field of Search ................ 128/774; 604/96–101

[56] References Cited

U.S. PATENT DOCUMENTS

| 3,707,146 | 12/1972 | Cook et al. | 128/2 R |
|---|---|---|---|
| 4,133,303 | 1/1979 | Patel | 128/774 |
| 4,160,446 | 7/1979 | Barrington | 604/96 |
| 4,349,033 | 9/1982 | Eden | 128/774 |
| 4,351,341 | 9/1982 | Goldberg et al. | 128/774 |
| 4,773,899 | 9/1988 | Spears | 604/96 |
| 4,819,751 | 4/1989 | Shimada et al. | 604/104 |
| 5,084,060 | 12/1992 | Freund et al. | 604/100 |
| 5,163,906 | 11/1992 | Ahmadi | 604/101 |

FOREIGN PATENT DOCUMENTS

| 0289021 | 2/1988 | European Pat. Off. | |
| 0409436 | 1/1991 | European Pat. Off. | 604/96 |

Primary Examiner—Max Hindenburg
Attorney, Agent, or Firm—Willian, Brinks, Hofer Gilson & Lione

[57] ABSTRACT

The present invention includes an imaging catheter for providing a three-dimensional representation of a body vessel wall. The imaging catheter includes an expandable deformable balloon which is inserted into a lumen of the body vessel at a position of interest on the vessel wall. After the balloon has been inflated, the balloon is then deflated and withdrawn from the body vessel to provide a three-dimensional image of the position of interest on the vessel wall.

20 Claims, 3 Drawing Sheets

IMAGING BALLOON CATHETER AND METHODS FOR USE AND MANUFACTURE

BACKGROUND OF THE INVENTION

1. Field of the Invention

The present invention relates to the field of angioplasty and, in particular, to an imaging catheter for insertion into a patient's vascular system to record and remember the configuration or shape of an obstruction therein.

2. Description of the Prior Art

Angioplasty has gained wide acceptance in recent years as an efficient and effective method for treating certain types of vascular diseases. In particular, angioplasty is widely used for expanding a constricted area or a lesion in a coronary artery. It is also used for treatment of lesions in other parts of the vascular system as well.

The most widely used form of angioplasty makes use of a balloon dilatation catheter which is introduced into a patient's vascular system and is positioned across a stenosis. The balloon is inflated by supplying fluid under pressure through an inflation lumen connected to the balloon. The inflation of the balloon imparts a stretching force to the stenosis or artery wall to reestablish an acceptable blood flow through the artery.

However, balloon dilatation is not always the method of choice for treating a stenosis within a coronary artery. Depending on the nature of the obstruction and other factors regarding the general condition of the patient, balloon dilatation may not be the preferred method for reestablishing the initial integrity of the artery. In fact, balloon dilatation can result in dissection of the artery wall. Other treatment methods for consideration include thrombolysis, atherectomy and laser ablation. Since balloon dilatation is not always the preferred procedure for reestablishing the flow of blood through an artery, it is essential that there be a method for examining the damage or obstruction. Having the capability to evaluate, among other things, the extent of artery disease and the length and eccentricity of a lesion allows a physician to choose the most effective method of treatment.

There are several known methods for examining an obstruction or stenosis for the purpose of evaluating the correct procedure for treatment. One such procedure, known as angiography, involves the examination of the obstructed blood vessel by radiography. Essentially, a radiopaque substance is introduced into a patient through the obstructed artery. With the aid of a fluoroscope, X-rays are used to examine the path of the radiopaque dye as it travels through the artery to the stenosis. A two-dimensional vision of the obstruction or stenosis is produced on the fluoroscope screen by the interaction of the X-rays with the radiopaque dye. A doctor may then examine this two-dimensional image for evaluating treatment.

Another method for imaging a lesion or stenosis in preparation of a revascularization procedure is through the use of intravascular ultrasound. The intravascular ultrasound also provides a two-dimensional cross-sectional image of the obstructed artery for examining the stenosis therein. With software enhancements, computer generated 3-D images can be generated but image quality is poor and the system cost is high.

Alternatively, European Patent Application 0289021 (Samson et al.) discloses another method of imaging, employing a plurality of optical fibers. The optical fibers are attached to a distal end of a catheter which is introduced into the obstructed artery. The optical fibers are positioned proximate to the obstruction to record and transmit an image of the obstruction so that it may be examined by a physician. This system requires the stoppage of blood flow and the introduction of clear saline into the artery for imaging. Imaging can therefore only be done for a short time and the system is difficult to pass through a tortuous coronary artery.

Although, several imaging systems have been described, there has been a continuing need to provide a simple, easy to use three-dimensional imaging system for the purpose of ascertaining the configuration of a cavity or lumen within a body. In particular, there is a need for such an imaging system for vascular applications to learn the configuration of an artery having an obstruction therein for the purpose of proposing and assessing treatment therefor. It would be advantageous if such an imaging system were available that is relatively easy to manufacture at a low cost and did not require capital support equipment.

SUMMARY OF THE INVENTION

The present invention relates to an imaging catheter which is introduced into a patient for the purpose of producing a three-dimensional image of a cavity or lumen into which the catheter has been inserted. The imaging catheter makes use of an expandable, deformable balloon which is carried at a distal end of the imaging catheter. The expandable balloon is inflated to deform to the shape of the body lumen or cavity to create a three-dimensional negative image thereof.

The imaging catheter has particular application for assessing the extent of vascular damage suffered by a patient. In such applications, the catheter is introduced into a patient's vascular system and advanced until the deformable expandable balloon is positioned across an obstruction or lesion in the patient's artery. An inflation device attached to the catheter at its proximal end outside of the patient is used to expand the balloon. The balloon is inflated to a first pressure which allows the balloon material to expand to correspond to the shape of the cavity or lumen to produce a negative image thereof. The balloon material is sized such that its maximum expanded diameter is slightly larger than the diameter of the native vessel. This prevents excess expansion into side branch vessels which could hinder later withdrawal. If the imaging catheter is used for vascular imaging applications, the first pressure is lower than a pressure that would dilate the lesion. Once inflated, the deformable balloon will set to the expanded shape and will maintain its expanded shape after the inflation pressure is withdrawn unless a further pressure is applied to further expand the balloon for a reorientating tensile force is applied. Thereafter, the balloon is deflated by application of vacuum and withdrawn from the patient. The deformed balloon is reinflated at a second pressure, which is lower than the first deforming pressure, to assume the previously deformed shape for examination. The second pressure is less than a pressure that would cause the balloon to further deform.

Further objects and advantages of this invention will become more apparent and readily appreciated from the following detailed description of the present invention with reference to the accompanying drawings.

DETAILED DESCRIPTION OF THE PREFERRED EMBODIMENT

Figures 1, 2:
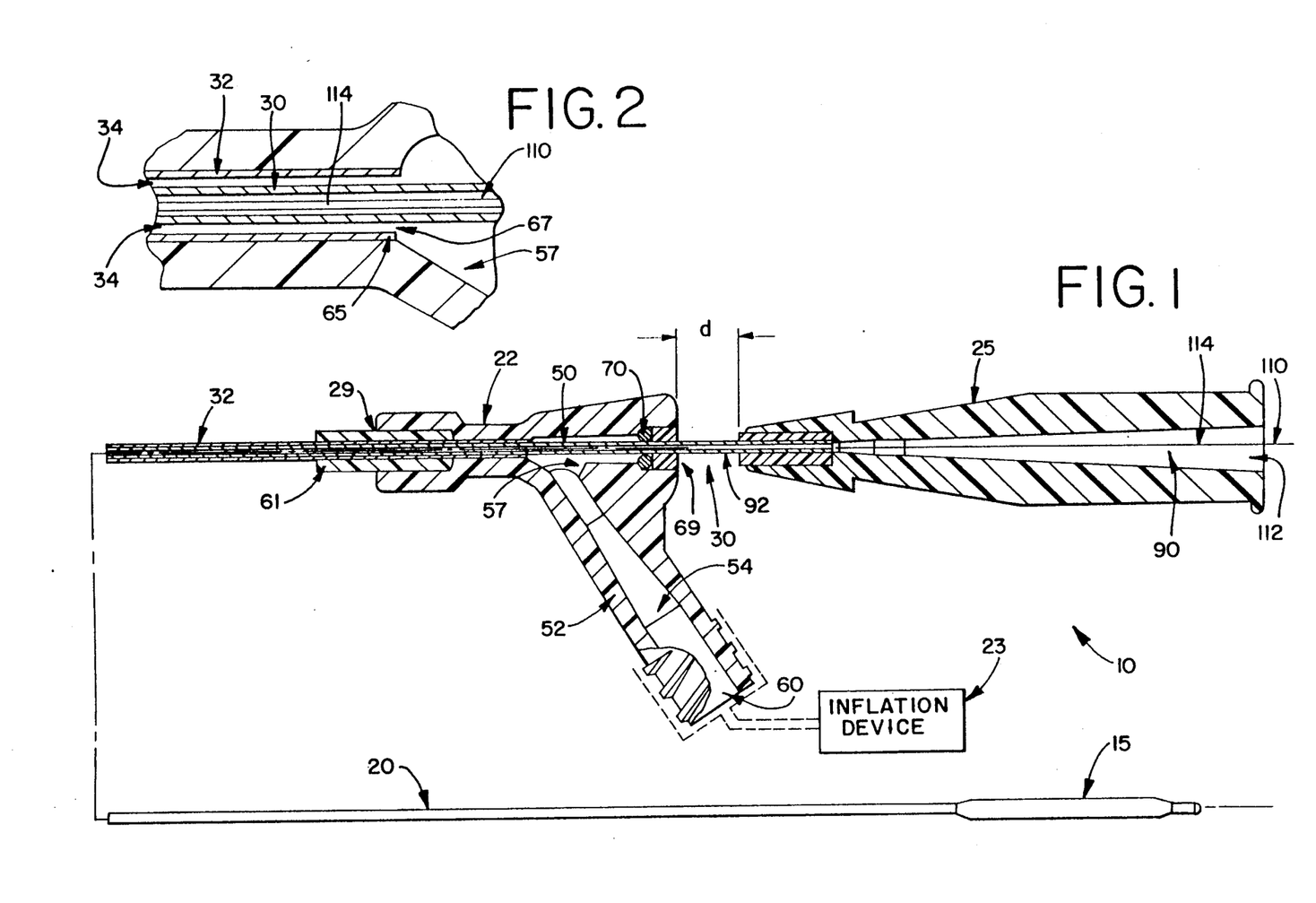
FIG. 1 is a side elevation view, in partial cross-section, of a balloon imaging catheter of the present invention.
FIG. 2 is an enlarged cross sectional view of a portion of the balloon manifold as illustrated in FIG. 1.

The present invention relates to an imaging balloon catheter generally indicated in FIG. 1.

As illustrated in FIG. 1, the balloon-type imaging catheter 10 comprises a shaft 20, a first manifold 22 and a second manifold 25. The shaft 20 extends distally from a distal end opening 29 of the first manifold 22 to a balloon 15. The shaft 20 is formed of an inner tube 30 and an outer tube 32, with the outer tube 32 coaxially disposed about the inner tube 30 to define an annular inflation lumen 34 therebetween as illustrated in FIG. 2. The inner tube 30 and the outer tube 32 are preferably constructed of a polymeric material such as polyethylene.

The first manifold 22 is preferably formed of a polycarbonate material and includes a central bore 50 extending therethrough and an inflation leg 52. The inflation leg 52 has an inflation channel 54 fluidly connected to the central bore 50 at a juncture 57. The inflation leg 52 has a threaded end 59 adapted to receive an inflation device 23 which is depicted schematically. An inflation medium, such as saline solution, is introduced under pressure into the inflation channel 54 through an entry port 60 on the inflation leg 52. The inflation device 23 is a conventional device such as the "SM 2000" available from SciMed Life Systems, Inc. of Maple Grove, Minn.

The outer tube 32 and the inner tube 30 extend proximally through the distal end opening 29 of the first manifold 22. Preferably, a strain relief member 61 is interposed between the outer tube 32 and the first manifold 22 at the distal end opening 29 to help ensure the mechanical security of the assembly and prevent kinking. Inner tube 30 extends through the central bore 50 while the proximal end 65 of the outer tube 32 terminates distally of the inflation channel 54 to define an inlet 67 to the inflation lumen 34 between the inner tube 30 and the outer tube 32 as illustrated in FIGS. 1 and 2. The proximal end 65 of the outer tube 32 is secured to an inner surface of the balloon manifold 22 by suitable means, such as an epoxy bond. Inflation medium is introduced from the inflation device 23 into entry port 60 and through the inflation channel 54 where the inflation medium is directed into the inflation lumen 34 through the inlet 67 at the proximal end 65 of the outer tube 32. The inflation medium then travels through the inflation lumen 34 to inflate the balloon 15 at the distal end of the catheter 10.

The inner tube 30 extends proximally beyond the juncture 57 through a proximal end opening 69 of the first manifold 22. The proximal end opening 69 is fluidly sealed by the cooperation of a deformable O-ring 70 through which the inner tube 30 is disposed. The relationship of the deformable O-ring 70 and the inner tube 30 at the proximal end opening 69 permits the inner tube 30 to move longitudinally relative to the outer tube 32 which is fixed at the juncture 57 by suitable means such as an epoxy. The purpose for providing longitudinal movement will be described in detail with respect to the operation of the catheter.

The second manifold 25 is also preferably formed of a polycarbonate material. Manifold 25 includes a central bore 90 and a distal end opening 92 designed to receive the inner tube 30. A guide wire 110 is introduced through a proximal end opening 112 of the second manifold 25 into a guide wire lumen 114 defined through the inner tube 30 as shown in FIGS. 1 and 2. The guide wire 110 extends distally through the guide wire lumen 14 and through a distal end opening 115 (shown in FIGS. 3–6) of the inner tube 30 to aid and assist the introduction of the catheter 10 into the patient and the advancement thereof across the lesion. Alternatively, a fixed wire design can be used whereby the inner lumen 30 is replaced by a wire element.

Figure 3:
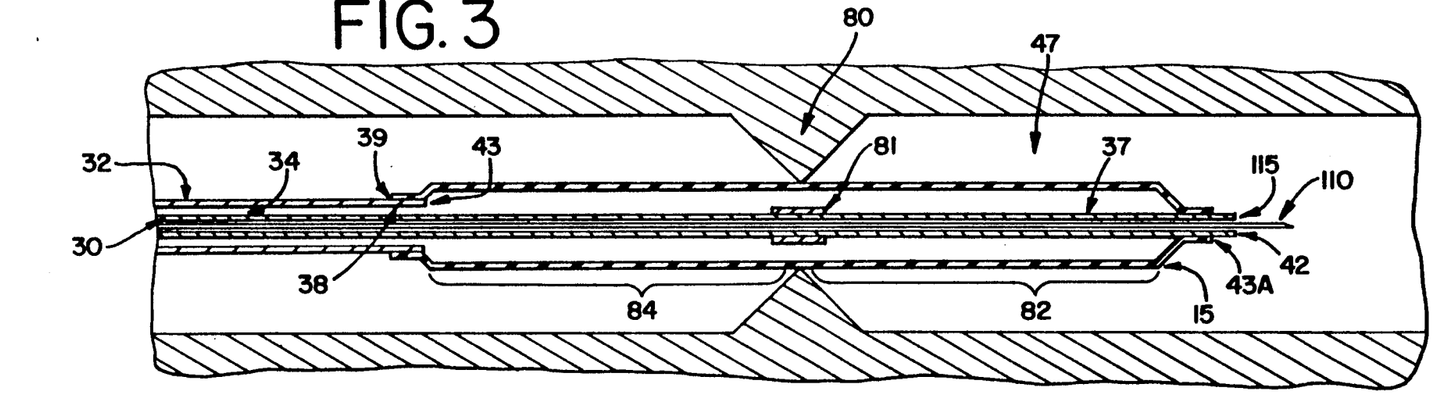
FIG. 3 is a diagrammatic sectional view of a distal portion of the balloon imaging catheter of FIG. 1, with the balloon illustrated in a deflated, nonexpanded condition and positioned across an obstruction in a vessel.

As illustrated in FIG. 3, the inner tube 30 extends distally beyond a distal end 38 of the outer tube 32. The formable balloon 15 extends coaxially over a distal end portion 37 of the inner tube 30. The entire balloon 15 including its proximal end 39 and its distal end 40 is preferably formed from a blend of polybutylene terephthalate and polyethylene terephthalate glycol. The proximal end 39 of the balloon 15, is bonded to the distal end 38 of the outer tube 30 at 43. A distal end 40 of the balloon 15 is bonded to a distal end 42 of the inner tube 30 at 43A to define the balloon cavity 47, which is in fluid communication with the inflation lumen 34. Preferably, an epoxy adhesive is used to bond the balloon 15 to the distal ends 43 and 43A of the outer and inner tubes respectively.

The imaging catheter is designed for insertion into a body cavity or lumen of a patient for the purpose of producing a three-dimensional negative image of the lumen. In particular, the imaging catheter 10 is useful for evaluating the condition of a patient's vascular system and any blockage therein and assessing treatment options or results. In addition the imaging catheter 10 is particularly valuable in choosing a properly sized device to treat the condition. The imaging catheter 10 includes a deformable, expandable balloon 15 designed to conform to the shape of a lesion or obstruction when positioned across the lesion or obstruction and expanded by a radial expansion pressure. The balloon 15 is positioned at a distal end of the catheter 10 and is adapted to receive an inflation medium for expansion.

In order to achieve the imaging feature of the catheter 10, the balloon 15 must be formed of a material which is expandable upon the application of a radial expansion pressure. In application, this expansion pressure must be significantly lower than the pressure sufficient to dilate the lesion so that the balloon molding or imprinting feature of the present invention is accomplished. Furthermore, the balloon 15 must "remember" the expanded shape so that after the expansion pressure is released and the balloon 15 is withdrawn and reinflated, the reinflated balloon 15 expands to the previously deformed shape of the obstruction "remembered" for analysis.

A balloon 15 exhibiting the necessary material characteristics may be formed of an orientable polymeric material. It has been discovered that a blend of polybutylene terephthalate (PBT) and polyethylene terephthalate glycol (PETG) material, referred to as PBT/PETG, provides a balloon with the desired permanent imaging deformation characteristics. The desired blend of PBT/PETG is formed of approximately 90-50% (by weight) polybutylene terephthalate (PBT) and 10-50% (by weight) polyethylene terephthalate glycol (PETG) or otherwise a ratio of PBT to PETG of between 9:1 and 1:1 by weight.

Unmodified PBT is a semicrystalline, high molecular weight thermoplastic material. Unmodified PBT refers to the grade of PBT in which no filler material such as fiberglass or mineral has been added. Celanex 1600A, a PBT available from Hoechst Celanese Corporation, has a melt index of 6.7 grams/10 min. and an intrinsic viscosity of 1.2 dl/g. Celanex 1700A, an ultrahigh molecular grade of PBT available from Hoechst Celanese Corporation, has a melt index of 4.1 grams/10 min. and an intrinsic viscosity of 1.4 dl/g. Original pellets of the 1600A and 1700A PBT's were tested and found to have a glass transition temperature ($T_g$) of 35°-40° C. temperature ($T_m$) of 224° C. and 211° C. respectively and a degree of crystallinity of 40-50%.

Kodar PETG copolyester 6763, a clear, amorphous PETG polymer available from Eastman Kodak Company, is a glycol-modified polyethylene terephthalate (PET). The modification is made by adding a second glycol, cyclohexandedimethanol (CHDM) during the polymerization stages. The second glycol is added in the proper proportion to produce an amorphous polymer. (The name PETG is an abbreviation given by Eastman Kodak Company and may not be industrially known.) PETG 6763 will not crystallize and thus offers wider processing latitude than conventional crystallizable polyesters. PETG 6763 has an intrinsic viscosity of 0.8 dl/g and glass transition temperature ($T_g$) of 80° C.

There are at least two methods to blend PBT and PETG. The first method is to blend the raw resins with an extruder to make pellets with well-mixed composition. The blended pellet is then put through a second extruder from which tubing is extruded, as is well known in the art. The blending step results in good mixing characteristics, however, it also results in two heating histories, one during the blending of the pellets in the extruder and one during the extrusion of the tubing from the second extruder. Exposure to two heating histories may degrade the polymers.

The second method is to mix original pellets of PBT and PETG by machine or hand-shaking at room temperature. The mixture is then fed to an extruder and extruded into tubes. This second method is simpler than the first method. The resulting tubing may be more poorly mixed than the tubing resulting from the first method, however, because the polymers will have only been subjected to a single heating cycle in the extruder.

The following example is for illustrative purposes only, and should not be construed as limiting the present invention in any way.

EXAMPLE 1

The second method, pellet mixing at room temperature, was conducted using the C. W. Brabender Extruder (0.75 inch), type 2523. The extrusion conditions used in the experiments conducted are listed in Table I. The extruder used to conduct the experiment has two thermocouples to measure the melting temperature of the extrusion. The first thermocouple is located outside of the melt flow while the second thermocouple is located inside the melt flow. Therefore the two temperatures listed under the heading "Melting Temperature" refer to the temperature measured by the first and second thermocouple respectively. As would be expected, the second temperature is higher than the first since the second thermocouple is located in the melt flow. Thermal analysis results are listed in Table II. The glass transition temperature variation indicates the interactions and good compatibility between PBT and PETG.

As can be seen in Table II, three samples of PBT/PETG were prepared. Because of sufficient compatibility between PBT and PETG, phase separation is unlikely to occur in the blends. As indicated in the results shown in Table II, the melting temperature of PBT remains unchanged in the blends, which suggests that amorphous PETG will not change the regularity of the PBT crystalline structure and that the amorphous PETG does have a good compatibility with amorphous portions of PBT.

TABLE I

| Comp. of Blends | Extrusion Conditions of PBT/PETG Blends | | | | | | | |
|---|---|---|---|---|---|---|---|---|
| | Temperature °C. | | | | | | Melting | |
| % PBT/% PETG | Zone 1 | Zone 2 | Zone 3 | Zone 4 | Zone 5 | Zone 6 | Pressure | Temperature |
| 100/00 | 210 | 235 | 235 | 240 | 245 | 250 | 1363 psi | 234/261° C. |
| 90/10 | 210 | 220 | 230 | 226 | 240 | 248 | 2002 psi | 227/248° C. |
| 80/20 | 210 | 224 | 227 | 232 | 232 | 235 | 1668 psi | 226/249° C. |
| 70/30 | 210 | 224 | 227 | 232 | 232 | 235 | 1726 psi | 226/249° C. |

TABLE II

| | Thermal Analysis of PBT/PETG Blends | | | |
|---|---|---|---|---|
| Comp. of | Temperature °C. | | | Melting |
| Blends % PBT/ % PETG | $T_g$ (glass) | $T_m$ (melting) | $T_c$ (crystallization) | Enthalpy, ΔH g/J |
| 90/10 | 37 | 222 | 173 | 56 |
| 80/20 | 40 | 222 | 168 | 43 |
| 70/30 | 48 | 222 | 162 | 37 |

The formation of the balloon 15 is a multistep process. First, a portion of the extruded PBT/PETG tube is "isolated." This isolated portion will become the balloon 15 by applying a tensile force to the ends of the PBT/PETG tube at room temperature. The tensile force progressively affects the molecular structural orientation of the tube starting from each end of the tube where the force is applied. The force progressively travels along the length of the tube away from each end towards the "isolated" portion to create uniaxially oriented portions. The isolated portion, however, will not have become uniaxially oriented because the tensile force is removed before the isolated portion has become affected. This process is commonly referred to as "necking" the tubing and is well known by those skilled in the art.

Next, the isolated portion is radially expanded by applying pressure and heat to the tubing. The pressure may be in the range of 40-100 psi, for example, and the temperature may be between 50°-90° C. The radial expansion and simultaneous longitudinal tension caused by further tension on the ends of the tube results in biaxial orientation in the isolated portion. While the isolated portion radially expands under these conditions, the uniaxially oriented portions do not.

Next, longitudinal tension is applied to the expanded, isolated portion to draw down the isolated portion. The longitudinal tension also reduces the diameter of the isolated portion, thereby reducing the balloon's profile. The length of the isolated portion increases correspondingly with the diameter profile reduction and is significantly longer than the original untreated length. Stretch values may range from 45% to a 100% increase in length. Pressure can be applied again to the tubing to reform the expanded isolated portion and then tension can be applied again to draw down the expanded portion until the isolated portion corresponds to a balloon of desired dimension. The thickness of the fully expanded balloon wall will preferably range from approximately 0.0004-0.0015 inches and most preferably from 0.0005-0.00075 inches.

Figure 4:
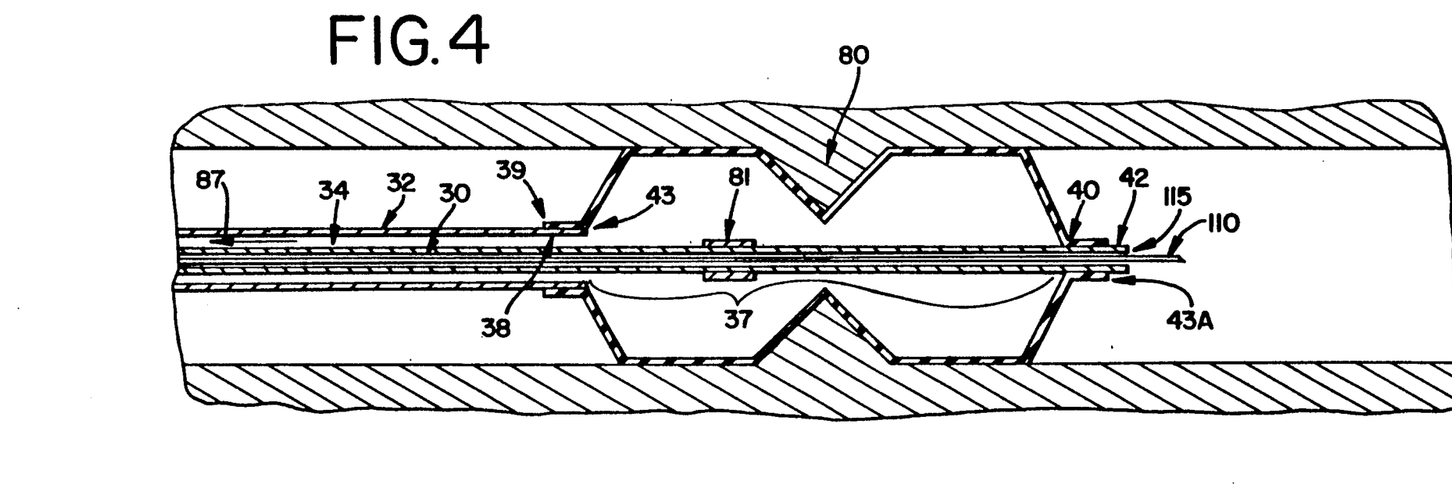
FIG. 4 is a diagrammatic sectional view similar to FIG. 3 with the balloon illustrated in an inflated, deformed condition.

During use of the balloon 15 for vascular applications as illustrated in FIGS. 3 through 6, the imaging catheter 10 of the present invention is introduced into a lumen such as a patient's artery and advanced until the balloon 15 is positioned across a stenosis or obstruction 80. Once in position, as best illustrated in FIG. 3, an inflation medium such as a mixture of renegrafin 76/saline (50/50) is used to inflate the balloon 15 at a first inflation pressure, thereby deforming the balloon 15 to the shape of the stenosis 80. The inflation medium is introduced through the entry port 60 of the first manifold 22. The first pressure is sufficient to permanently deform the balloon 15 in its most expanded state, thus forming a three-dimensional negative image of the lesion or obstruction 80 in the patient's artery as shown in FIG. 4.

Figure 5:
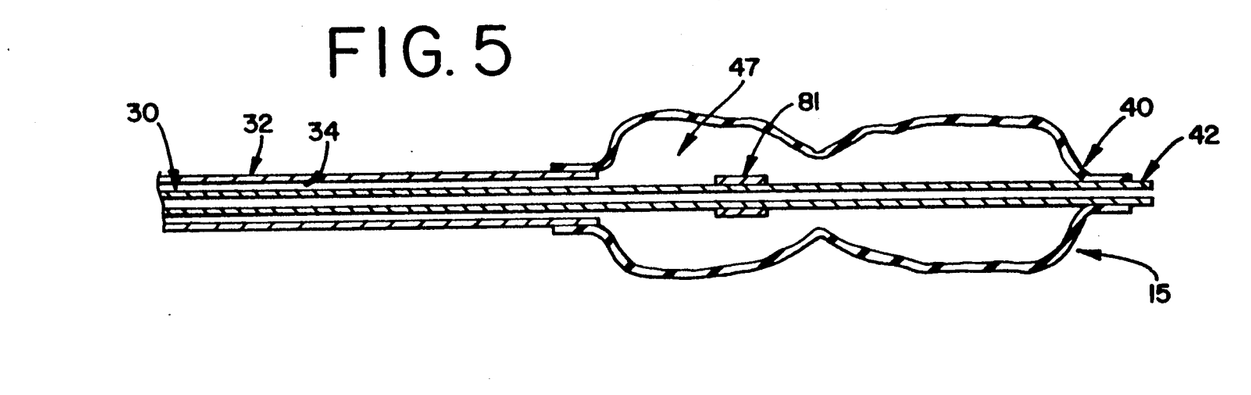
FIG. 5 is a diagrammatic sectional view of the deformed balloon of FIG. 4, which has been deflated and withdrawn from the patient.
Figure 6:
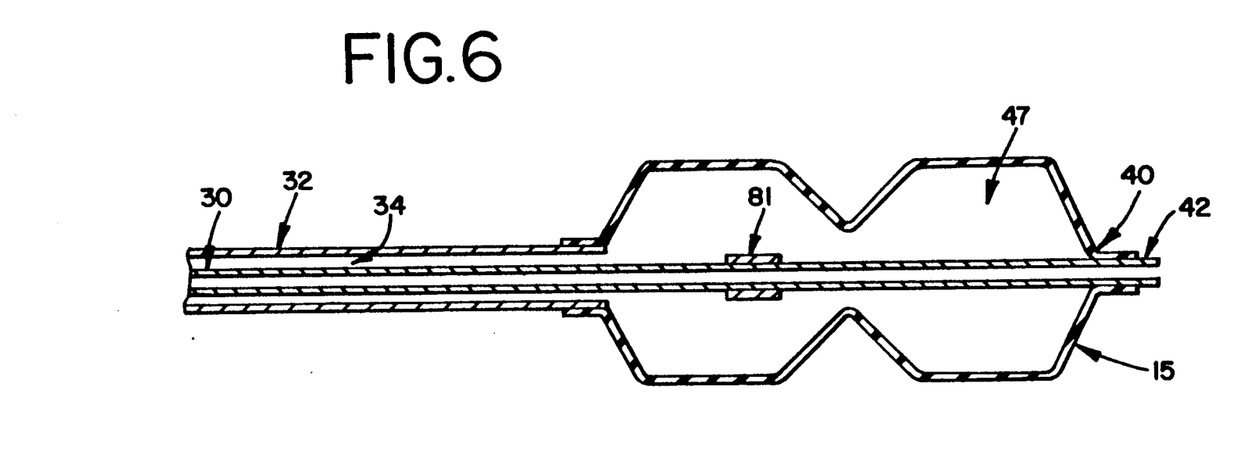
FIG. 6 is a diagrammatic sectional view of the deformed balloon of FIG. 5, reinflated for analysis.

The balloon 15 is then deflated by applying a vacuum so that the imaging catheter 10 may be withdrawn from the patient for analysis as illustrated in FIG. 5. After the imaging catheter 10 is withdrawn, the balloon 15 is reinflated at a second pressure which is less than the first inflation pressure. The lower reinflation pressure permits the balloon 15 to assume its originally deformed shape of the obstruction or lesion without further deformation as illustrated in FIG. 6. Thereafter, the balloon 15 is examined to evaluate the extent of constriction or damage present in the patient's lumen to determine treatment options and procedures.

After a treatment option has been selected and used, the balloon catheter can be reintroduced into the vascular system to provide an image of the lumen after treatment. This aids the physician in determining whether the treatment was successful.

As explained earlier, the balloon 15 will radially expand upon the application of a first inflation pressure. The inflation pressure can range from approximately 2-7 atm., (30-100 psi), and will preferably be between 2.3 atm., (40 psi). A corresponding reduction in the length of the balloon 15, however, accompanies the radial expansion. The first inflation pressure causes the balloon 15 to expand and retain its expanded shape at this pressure. The balloon 15 will remember the shape after the inflation pressure is released unless a reorientating tensile force is applied or additional pressure is applied to further deform the balloon 15. A radiopaque marker band 81 made from a platinum alloy is bonded with adhesive to the inner tube 30 under the balloon to indicate to the physician the center position of the unexpanded balloon segment. The marker has a typical wall thickness of about 0.0015" to 0.0020" and a length of about 0.060" to 0.080".

With reference to FIGS. 3 and 4, when the balloon 15 is positioned across the stenosis 80, ideally, a first portion of the balloon 82 extends distally beyond the stenosis 80 and a second portion 84 extends proximally thereof. When the balloon 15 is inflated as illustrated in FIG. 4, the axial length of the balloon 15 shortens coincidentally with radial expansion. A comparison of FIGS. 3 and 4, in which the balloon is drawn to the same scale, illustrates the shortening of the balloon 15.

To accommodate for the shortening of the axial length of the expanded balloon 15 without disturbing the position of the balloon 15 with respect to the stenosis 80, both the inner tube 30 and the outer tube 32 are adapted to move relative to one another. Specifically, the inner tube 30 is adapted to slide in the proximal direction as indicated by arrow 87 in FIG. 4 relative to the outer tube 32 to accommodate for the shortening in the first portion 82 of the balloon 15. Thus, to facilitate the relative movement of the inner tube 30 and the outer tube 32, the inner tube 30 is adapted to slide proximally through the seal of the O-ring 70 to adjust the length of the inner tube 30 extending beyond the proximal end opening 69 of the first manifold 22. Accordingly the distance between the first manifold 22 and the second manifold 25 is adjusted a distance "d" as illustrated in FIG. 1.

Unique balloon properties of the PBT/PETG blends, such as the reverse deformation with memory, may be due to the unique crystalline structure of the PBT material. Allomorphs, which undergo a unique, reversible transformation at low levels of applied stress, have been reported for PBT. The term "allomorphs" refers to any of two or more distinct crystalline forms of the same substance. One phase ($\alpha$), is always present in an unstressed oriented state and transforms to a different phase ($\beta$) when the material is stressed. The original $\alpha$-phase returns when the stress is released. The transformation of the $\alpha$-phase to $\beta$-phase is complete when the sample of the $\alpha$-form is stretched about 10-12%. This behavior is attributed to a conformational change of the tetramethylene chain from a relaxed gauche-trans-gauche to a stretched all-trans form and involves a small change in enthalpy and volume. Both phases have been characterized as having a triclinic unit-cell structure.

It should be recognized that alternative materials which have characteristics such as those described above may be used to form the balloon 15 in order to achieve the molding feature of the present invention. For example, PBT may be used in an unblended state, however, a higher pressure is needed to inflate the tubing and the material crystallizes sooner than a blend of PBT and PETG. The role of the amorphous PETG in the blends is to make the balloon forming process easier.

The following examples and embodiments are for illustrative purposes only, and should not be construed as limiting the present invention in any way. Example 2 describes the formation of the balloon material. Examples 3, 4 and 5 describe the final formation and use of the balloon made according to Example 2.

EXAMPLE 2

Blend 70% (by weight) of polybutylene terephthalate (PBT) with 30% (by weight) of glycol-modified polyethylene terephthalate (PETG) by mixing original pellets of PBT and PETG at room temperature as described above. Use Celanex 1600A for the PBT and Kodar PETG 6763 for the PETG as described above.

Extrude PBT/PETG tubes from the blend using a C. W. Brabender Extruder (0.75 inch), type 2523 having an extrusion profile shown in Table III.

TABLE III

| Comp. of Blends | Extrusion Conditions | | | | | | | |
|---|---|---|---|---|---|---|---|---|
| | Temperature °C. | | | | | | Melting | |
| % PBT/% PETG | Zone 1 | Zone 2 | Zone 3 | Adapter | Helicoid | Die | Pressure | Temperature |
| 70/30 | 236 | 232 | 228 | 224 | 224 | 270 | 3100 psig | 238° C. |

Since the extrusion temperature profile is not critical to the present invention, other extrusion temperature profiles may be substituted.

Use the following dimensions of the tooling instruments:

| | |
|---|---|
| die | .065" |
| mandril | .057" |
| hypo tube | .056" |
| screen | none |

Cut the tubing into many tube sections, and mark a length of 1 cm on each tube section for reference in the isolated portion. Thus, form an isolated portion of the extruded tube in the tubing by applying tension to the ends of one of the tube sections to create uniaxially oriented portions as described above in Example 1.

EXAMPLE 3

Inflate the tubing section at a pressure ranging from 60–100 psig in a water bath with a temperature between 50° C. and 90° C. At 60° C., the balloon should be preferably inflated at a pressure between 60 and 100 psig and most preferably between 80 and 100 psig. At 80° C., the balloon should be preferably inflated at a pressure of between 40 and 60 psig and most preferably at 50 psig. Stretch the deflated tube preferably in the range of 1.5-2 times its length preferably with a stretch ratio of 8.2-0. Inflate the balloon in an artery between the range of 40 and 80 psig and most preferably between 40 and 60 psig. The inflation pressure should not exceed 60 psig to avoid yielding the area being molded when the balloon is used in a vascular system. Reinflate the balloon at a pressure preferably ranging between about 5 and 20 psig and most preferably between 5 and 10 psig for a period ranging for at least 10 seconds and preferably at least 30 seconds.

EXAMPLE 4

Apply a pressure of 50 psig to the tubing section. Place the tubing section in a 70° C. water bath. Remove the tubing section from the bath. Remove the pressure and apply longitudinal tension to the ends of the tube to draw the tube down approximately 2 times its deflated length.

Place a clamp on the balloon to simulate an obstruction in the vascular system. Inflate the balloon at a pressure of 40 psig and temperature of 37° C. for a period of 60 seconds. Deflate the balloon and remove the clamp. Reinflate the balloon at a pressure 20 psig at room temperature.

EXAMPLE 5

Several embodiments of the tubing formed according to Example 2 as described above were tested with varying parameters as illustrated in Table IV. The extruded tube had an inner diameter of 0.036" and an outer diameter of 0.043" with a wall thickness ranging from 0.00335" to 0.00375". The wall thickness varied because the cylindrical bore in the tube was not centered. When the "isolated" portion of the extruded tube was exposed to a pressure and temperature to radially expand the isolated portion, the 1 cm marked length increased to approximately 2.5 cm. When the pressure was removed, the length of the tube slightly decreased.

In embodiments A–L, a tubing section with an isolated portion was inflated to a particular pressure ranging from about 26–100 psig and then placed in a 80° C. water bath. In embodiment K, the stretching could not be controlled and thus resulted in a very small and thus unusable balloon. It is believed that the inflation pressure of 26 psig was not sufficient. In embodiment L, the balloon burst while being inflated at 100 psig. It is believed that the inflation pressure was excessive. The tubes in embodiments A–J were then stretched approximately 45–70% times its length.

In embodiments A–J, the imaging property of the balloon was then tested by placing a clamp on the balloon to simulate an obstruction in the vascular system. The balloon was inflated at pressures ranging from 40–100 psig at a temperature ranging from 21°–37° C. for a period of time ranging from 5–120 seconds. In embodiment J, the tube burst while being inflated at 100 psig. It is believed that this was due to exceeding the burst pressure. It was found that the average burst pressure of a balloon formed according to embodiment J ranged approximately from 80–85 psig.

In embodiments A–I, the tube was then deflated and the clamp removed. The balloon was reinflated at a pressure ranging from 5–60 psig and a temperature of 25° C. In embodiments A–H the balloon successfully "remembered" the shape it had when the balloon was inflated with the clamp in place. It was found in embodiments F–H that the balloon would forget its shape if the balloon was reinflated at a pressure greater than about 25 psig when the clamp was removed. In embodiment I, the balloon did not "remember" its shape. It is believed that this was due to a short inflation period of 5 seconds compared with the inflation periods of 120 seconds used in embodiments A–H.

In embodiments M–P, a tubing section with an isolated portion was inflated to a particular pressure ranging from about 60–100 psig and then placed in a 60° C. water bath. The tube was then stretched approximately 50-180% times its length. In embodiment P, the stretching of the isolated segment could not be controlled thus resulting in a very small and unusable tube. It is believed that the initial pressure of 60 psig was not sufficient.

In embodiments M-O, the imaging property of the balloon was then tested by placing a clamp on the balloon to simulate an obstruction in the vascular system. The balloon was inflated at pressures ranging from 80-100 psig at a temperature of 37° C. for a period of 120 seconds.

The tube was then deflated and the clamp removed. The balloon was reinflated at a pressure ranging from 10-50 psig and a temperature ranging from 25°-37° C. In embodiment O, the balloon did not "remember" its shape. It is believed that the reinflation pressure of 50 psig was excessive. In embodiments M and N, the balloon successfully "remembered" the shape it had when the balloon was inflated with the clamp in place.

While the invention has been shown and described in connection with a particular preferred embodiment, it is apparent that certain changes and modifications, in addition to those mentioned above, may be made by those who are skilled in the art without departing from the basic features of the present invention. Accordingly, it is the intention of the Applicants to protect all variations and modifications within the true spirit and value scope of the invention.

TABLE IV

|  | A | B | C | D | E | F | G | H |
|---|---|---|---|---|---|---|---|---|
| 1st Inflation: | | | | | | | | |
| P (psig) | 60 | 40 | 44 | 50 | 50 | 50 | 50 | 50 |
| T (°C.) water bath | 80 | 80 | 80 | 80 | 80 | 80 | 80 | 80 |
| Outer diameter (mm) | 5.332 | 4.03 | 4.27 | 4.88 | 4.94 | 4.78 | 4.78 | 4.58 |
| Wall thickness (in) | .00047 | .0008 | ~ | ~ | .00051 | .00051 | .00051 | .00051 |
| Stretch | 45% | 50% | 70% | 50% | 65% | 60% | 50% | 50% |
| 2nd Inflation: w/clamp in place | | | | | | | | |
| P (psig) | 100 | 100 | 100 | 50 | 40 | 50 | 50 | 80 |
| T (°C.) | 21 | 21 | 21 | 37 | 37 | 37 | 37 | 37 |
| Time (sec) | 120 | 120 | 120 | 120 | 120 | 120 | 120 | 120 |
| 3rd Inflation: clamp removed | | | | | | | | |
| P (psig) | 20 | 10 | 10 | 10 | 10 | 10 | 10 | 5 |
| T (°C.) | 25 | 25 | 25 | 25 | 25 | 25 | 25 | 25 |

|  | I | J | K | L | M | N | O | P |
|---|---|---|---|---|---|---|---|---|
| 1st Inflation: | | | | | | | | |
| P (psig) | 42 | 50 | 26 | 100 | 100 | 80 | 60 | 60 |
| T (°C.) water bath | 80 | 80 | 80 | 80 | 60 | 60 | 60 | 60 |
| Outer diameter (mm) | 4.1 | 4.5 | 2.65 | ~ | 5.3 | 4.85 | 4.14 | 3.94 |
| Wall thickness (in) | .0008 | .00051 | ~ | ~ | ~ | .0006 | .0008 | .0009 |
| Stretch | 50% | 50% | 400% | ~ | 100% | 50% | 180% | ~ |
| 2nd Inflation: w/clamp in place | | | | | | | | |
| P (psig) | 100 | 100 | ~ | ~ | 100 | 80 | 80 | ~ |
| T (°C.) | 37 | 37 | ~ | ~ | 37 | 37 | 37 | ~ |
| Time (sec) | 5 | 50 | ~ | ~ | 120 | 120 | 120 | ~ |
| 3rd Inflation: clamp removed | | | | | | | | |
| P (psig) | 60 | ~ | ~ | ~ | 10 | 10 | 50 | ~ |
| T (°C.) | 25 | ~ | ~ | ~ | ~ | 25 | 25 | ~ |

What is claimed is:

1. A catheter comprising:
    a shaft adapted for insertion into a vascular system, said shaft having a distal portion and a fluid passageway that communicates with said distal portion; and
    an expandable tubular element mounted on the distal end of said shaft and in fluid communication with said fluid passageway to conform to the shape of the vessel when said expandable tubular element is inflated at a first pressure,
    said expandable tubular element constructed of a material that conforms to the shape of the vessel when said balloon is inflated at a first pressure and maintains the shape of the vessel after said balloon has been deflated and removed from the vascular system and reinflated at a second pressure.

2. A catheter according to claim 1 wherein said first pressure is greater than said second pressure.

3. A catheter according to claim 1 wherein said first pressure is less than a lesion deforming pressure.

4. A catheter according to claim 3 wherein the ratio of glycol-modified polyethylene terephthalate to polybutylene terephthalate is 3:7 by weight.

5. A catheter according to claim 1 wherein said first pressure ranges between 40 and 100 psig.

6. A catheter according to claim 1 wherein said first pressure ranges between 40 and 80 psig.

7. A catheter according to claim 1 wherein said first pressure ranges between 40 and 60 psig.

8. A catheter according to claim 1 wherein said second pressure ranges between 5 and 25 psig.

9. A catheter according to claim 1 wherein said second pressure ranges between 5 and 10 psig.

10. A catheter according to claim 1 wherein said expandable tubular element is constructed of a blend of polybutylene terephthalate (PBT) and glycol-modified polyethylene terephthalate (PETG).

11. A catheter according to claim 10 wherein the ratio of glycol-modified polyethylene terephthalate to polybutylene terephthalate ranges from 1:1 to 1:9 by weight.

12. A catheter according to claim 1 wherein said expandable tubular element material is a polymeric material that has been biaxially oriented.

13. A method for imaging a body vessel lumen, the method comprising:

providing an imaging catheter having an expandable balloon mounted at a distal end, the balloon being characterized by an ability to conform to the shape of the vessel wall upon inflation, and return to the conformed shape after deflation and reinflation;

advancing the imaging catheter into the body lumen to an imaging position;

inflating the balloon so that the balloon is forced against the vessel wall and conforms to the shape of the vessel wall;

deflating the balloon and withdrawing the balloon from the lumen; and reinflating the balloon to expand the balloon to assume the balloon's previous shape that corresponds to the shape of the vessel wall thereby providing an image of the lumen.

14. A method according to claim 13 wherein said balloon is expanded at a first pressure within the lumen and then reinflated at a second pressure after being withdrawn from the lumen wherein said first pressure is greater than said second pressure.

15. A method according to claim 14 wherein the body lumen has a lesion or obstruction and a balloon is positioned adjacent the lesion or obstruction such that when the balloon is inflated, the balloon deforms to the shape of the lesion or obstruction.

16. A method according to claim 15 wherein the balloon is inflated to a pressure that will not deform the lesion or obstruction.

17. A method according to claim 14 wherein the balloon is constructed of a blend of polybutylene terephthalate and polyethylene terephthalate glycol.

18. A method according to claim 17 wherein the ratio of glycol-modified polyethylene terephthalate to polybutylene terephthalate ranges from 1:1 to 1:9 by weight.

19. A catheter comprising:

a shaft adapted for insertion into a vascular system, said shaft having a distal portion and a fluid passageway that communicates with said distal portion; and an expandable tubular element mounted on the distal end of said shaft and in fluid communication with said fluid passageway to conform to the shape of the vessel when said expandable tubular element is inflated at a first pressure, said expandable tubular element constructed of a blend of polybutylene terephthalate (PBT) and glycol-modified polyethylene terephthalate (PETG).

20. A catheter to claim 19 wherein the ratio of glycol-modified polyethylene terephthalate to polybutylene terephthalate ranges from 1:1 to 1:9 by weight.

* * * * *

UNITED STATES PATENT AND TRADEMARK OFFICE
CERTIFICATE OF CORRECTION

PATENT NO. : 5,316,016
DATED : May 31, 1994
INVENTOR(S) : Daniel O. Adams et al.

It is certified that error appears in the above-indentified patent and that said Letters Patent is hereby corrected as shown below:

On the Title Page

In column 2, line 2 under "References Cited U.S. PATENT DOCUMENTS", delete "12/1992" and substitute --1/1992--.

Column 14,

In claim 20, line 1, after "catheter" insert --according--.

Signed and Sealed this

Twenty-fourth Day of October, 1995

Attest:

BRUCE LEHMAN

Attesting Officer    Commissioner of Patents and Trademarks